United States Patent [19]

Doub et al.

[11] 4,315,858

[45] Feb. 16, 1982

[54] ANTIBACTERIAL AMIDE COMPOUNDS

[75] Inventors: Leonard Doub, Tuscon, Ariz.; Theodore H. Haskell, Ann Arbor, Mich.; Thomas F. Mich, Ann Arbor, Mich.; Dietrich Schweiss, Ann Arbor, Mich.

[73] Assignee: Warner-Lambert Company, Morris Plains, N.J.

[21] Appl. No.: 190,128

[22] Filed: Sep. 24, 1980

[51] Int. Cl.³ .................. C07D 499/70; C07D 401/12; C07D 213/64
[52] U.S. Cl. .................................. 260/239.1; 424/263; 424/266; 546/276; 546/287; 546/288; 546/298
[58] Field of Search ...................... 260/239.1; 424/263, 424/266; 546/276, 287, 288, 298

[56] References Cited

U.S. PATENT DOCUMENTS

| | | | |
|---|---|---|---|
| 3,873,523 | 3/1975 | Daub et al. | 260/239.1 |
| 3,951,955 | 4/1976 | Tobiki et al. | 260/239.1 |
| 4,031,230 | 6/1977 | Gottschlich et al. | 424/263 |
| 4,092,309 | 5/1978 | Mich | 260/239.1 |
| 4,101,661 | 7/1978 | Kaltenbronn et al. | 424/266 |

Primary Examiner—Natalie Trousof
Assistant Examiner—Vera C. Clarke
Attorney, Agent, or Firm—Stephen Raines

[57] ABSTRACT

Novel organic amide compounds which are N-[6-(acylaminophenyl)-1,2-dihydro-2-oxonicotinoyl]-penicillin compounds having broad spectrum antibacterial utility are provided by (a) reacting the free amino acid of the appropriate penicillin or the acid salt or silylated derivative or complex thereof with a reactive derivative of the corresponding N-6-[acylaminophenyl]-1,2-dihydro-2-oxonicotinic acid or (b) reacting the free amino acid 6-aminopenicillanic acid or a related compound or the acid salt or silylated derivative thereof with a reactive derivative of the corresponding D-N-[6-[acylaminophenyl]-1,2-dihydro-2-oxonicotinoyl]-2-substituted glycine. Pharmaceutical compositions containing said compounds and methods for treating infections using said compositions are also disclosed.

18 Claims, No Drawings

ANTIBACTERIAL AMIDE COMPOUNDS

SUMMARY AND DETAILED DESCRIPTION

The present invention relates to novel chemical compounds that are useful as pharmacological agents and to methods for their production. More particularly, the invention relates to novel organic amide compounds having the formula

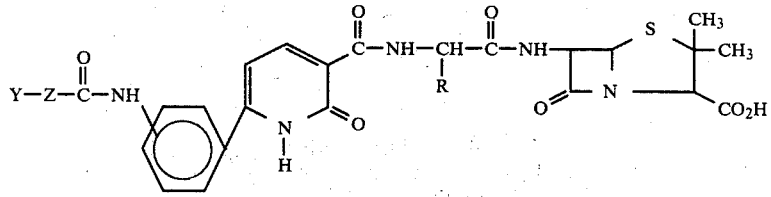

and pharmaceutically-acceptable salts thereof; wherein Z is a single bond and Y is lower alkyl, benzyl, $CF_3$, lower alkyl amino, lower alkyl carbonyl, lower alkoxy carbonyl, benzyloxy and lower alkoxy, where Z is a methylene group and Y is cyano, tetrazolyl, $R^1 CH_2S$ where $R^1$ is $CF_3$ or CN and R is phenyl, 4-hydroxyphenyl, 2-thienyl or cyclohexa-1,4-dien-1-yl.

The preferred compounds are those wherein

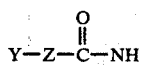

is in the p position and Z is a single bond, Y is methyl or where Z is methylene and Y is cyano and R is 4-hydroxyphenyl.

Lower alkyl is defined as a hydrocarbon fragment of from one to six carbon atoms.

In accordance with the invention the foregoing amide compounds having the formula

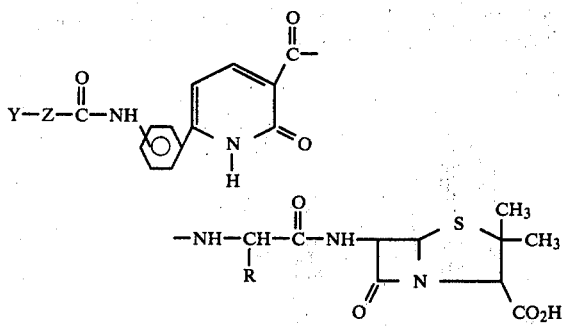

and pharmaceutically-acceptable salts thereof wherein Z, Y and R are as previously defined are produced by reacting a compound of the formula

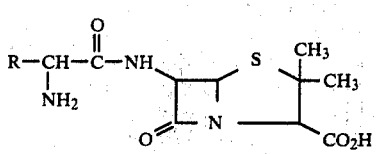

or the basic salt, silylated derivative (preferably the disilylated) or complex (preferably the dimethylsulfoxide) thereof wherein R is as previously defined, with a reactive derivative of a 1,2-dihydro-2-oxonicotinic acid compound having the formula

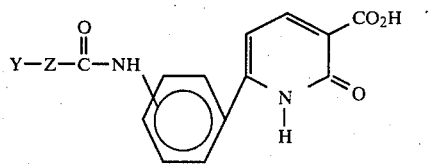

or its acid addition salt, where Z and Y all have the aforementioned significance.

Some examples of reactive derivatives of the 6-(substituted)-1,2-dihydro-2-oxonicotinic acid compound suitable for the reaction are the acid halides (especially the acid chloride), the imidazolide, mixed anhydrides (especially those formed from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (oxonicotinic acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin compounds in the free acid or salt form, aqueous solutions may be used for acylation with an acid halide or mixed anhydride under normal Schotten-Baumann conditions. The duration and temperature of the reaction are not critical. Temperatures in the range from −30° to +30° C. are commonly used for reaction times ranging from a few house up to a day or more. The product may by isolated in any suitable way as the free acid or as a salt by appropriate adjustment of the pH.

The reactive derivative of 6-(substituted)-1,2-dihydro-2-oxonicotinic acid compounds, which are required as starting materials in the foregoing process, can be prepared according to any of a variety of methods.

A 6-(substituted)-1,2-dihydro-2-oxonicotinic acid may be converted to its acid chloride utilizing thionyl chloride, its mixed anhydride utilizing ethyl chloroformate, its pentachlorphenyl ester by esterification with pentachlorophenol and its imidazolide by reacting the acid with 1,1′-carbonyl-diimidazole.

Compounds of the formula

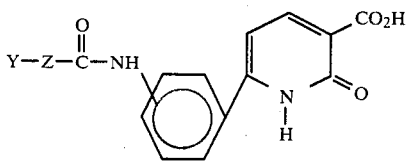

where Z and Y are as previously defined are prepared by acylation of a compound of the formula

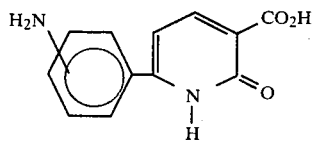

by a compound of the formula

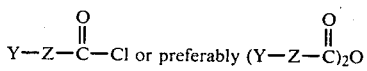

wherein Z and Y are as previously defined preferably with the aid of trimethylsilylchloride.

The compound of the formula

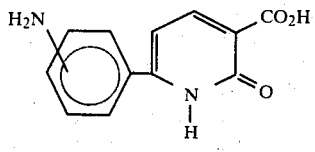

is prepared by hydrolyzing a compound of the formula

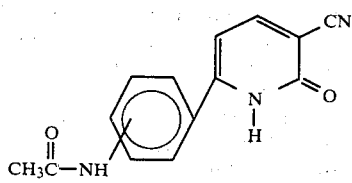

which is in turn prepared by coupling a compound of the formula

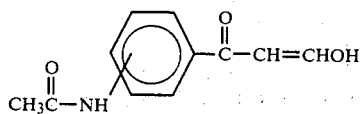

with 2-cyanoacetamide.

The compound of the formula

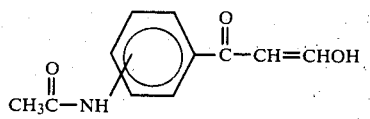

is prepared by formylating a compound of the formula

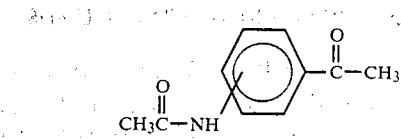

The silylated amino acid starting materials can be prepared by reacting an amino acid of the formula

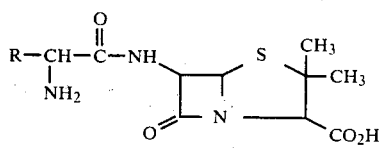

or a salt thereof wherein R is as previously defined in anhydrous form with either one or two equivalents of a tri(lower alkyl)silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono-and disilylated products are fully reactive with the activated acids. The disilyated product is preferred over the monosilylated product as a starting material. After acylation the silyl groups are easily removed by treatment with water.

Also in accordance with the invention, the compounds of this invention may be produced by reacting a free amino acid of the formula

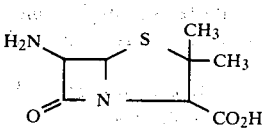

or the corresponding acid salt or silylated derivative thereof with a reactive derivative of D-N-[6-(substituted)-1,2-dihydro-2-oxonicotinoyl]-2-substituted glycine having the formula

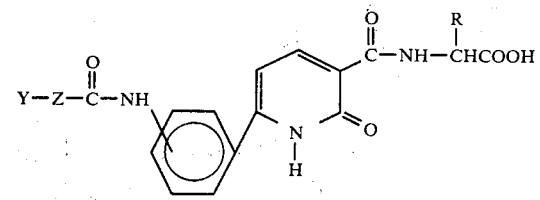

or its acid addition salts where Z, Y and R have the aforementioned significance.

Some examples of reactive derivatives of the D-N-(1,2-dihydro-2-oxonicotinoyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethyoxyethane), chlorinated hydrocarbons (such as chloroform and dichloromethane), and mixtures of these. In addition to any of these solvents, 6-aminopenicillanic acid may be reacted with an acid chloride or mixed anhydride in the free acid or salt form using aqueous solutions under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of D-N-[6-(substituted)-1,2-dihydro-2-oxonicotinoyl]-2-substituted glycines or their acid-addition salts which are required as starting materials in the foregoing process can be prepared by methods illustrated in greater detail hereinafter.

D-N-[6-(substituted-1,2-dihydro-2-oxonicotinoyl]-2-substituted glycine compounds may be prepared by reacting the corresponding reactive derivative of 6-(substituted)-1,2-dihydro-2-oxonicotinic acid, such as the acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

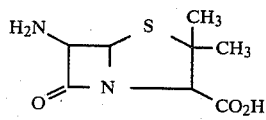

with a standard silylating agent such as chlorotrialkylsilane, hexaalkyldisilazane, etc. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically-acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention.

The compounds of the invention can exist in anhydrous form, as well as in solvated, including hydrated, forms. In general, the hydrated forms and the solvated forms with pharmaceutically-acceptable solvents are equivalent to the anhydrous or unsolvated forms for the purposes of the invention.

The pyridone segment of the compounds of this invention may be capable of undergoing keto-enol tautomerism to give 2-hydroxypyridines. Such a tautomer is equivalent to the pyridones for the purposes of the inventions and are included within the above shown structures.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their non-toxic pharmaceutically-acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg at about 1000 mg of active compound per unit dose form.

The invention is illustrated by the following examples.

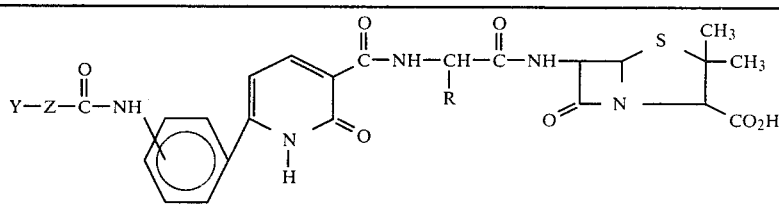

ACTIVITY TABLE
Minimal Inhibitory Concentration (μg/ml)

| Y—Z | Position | R | Pseudomonas aeruginosa #28 | Entero. cloacae | Serr. marces. | Klebs. pneu. | Staph. aureus S18713 |
|---|---|---|---|---|---|---|---|
| $CH_3$ | 3 | $C_6H_5$ | 6.3 | 6.3 | 12.5 | 3.1 | >200 |
| $CH_3$ | 4 | $C_6H_5$ | 3.1 | 12.5 | 25 | 6.3 | 100 |
| $CH_3$ | 4 | $4\text{-}HO\text{—}C_6H_4$ | 3.1 | 6.3 | 25 | 12.5 | 200 |
| $CF_3$ | 4 | $C_6H_5$ | 6.3 | 3.1 | 25 | 6.3 | 200 |
| $CF_3$ | 4 | $4\text{-}HO\text{—}C_6H_4$ | 1.6 | 3.1 | 100 | 3.1 | 100 |
| $CNCH_2$ | 4 | $4\text{-}HO\text{—}C_6H_4$ | 1.6 | 1.6 | 200 | 3.1 | 100 |
| $C_6H_5CH_2$ | 4 | $4\text{-}HO\text{—}C_6H_4$ | 1.6 | 1.6 | 50 | 3.1 | 50 |
| triazolyl-$CH_2$ | 4 | $4\text{-}HO\text{—}C_6H_4$ | 3.1 | 1.6 | 1.6 | 12.5 | >50 |
| $CF_3CH_2SCH_2$ | 4 | $4\text{-}HO\text{—}C_6H_4$ | 0.8 | 6.3 | 0.4 | 3.1 | >50 |
| $CNCH_2SCH_2$ | 4 | $4\text{-}HO\text{—}C_6H_4$ | 1.6 | 12.5 | 1.6 | 6.3 | >50 |
| $CH_3O$ | 4 | $4\text{-}HO\text{—}C_6H_4$ | 1.6 | 1.6 | 25 | 3.1 | 100 |
| $C_6H_5CH_2O$ | 4 | $C_6H_5$ | 1.6 | 6.3 | 12.5 | 0.8 | 50 |
| EtNH | 4 | $4\text{-}HO\text{—}C_6H_4$ | 0.8 | 3.1 | 0.8 | 6.3 | 50 |
| $CH_3C(O)$ | 4 | $4\text{-}HO\text{—}C_6H_4$ | 1.6 | 3.1 | 3.1 | 12.5 | 25 |
| EtOC(O) | 4 | $4\text{-}HO\text{—}C_6H_4$ | 6.3 | 1.6 | 200 | 6.3 | 50 |

EXAMPLE 1

N-[6-[4-(Acetylamino)phenyl]-1,2-dihydro-2-oxonicotinoyl]-ampicillin

A mixture of 11.5 g (50 mmol) of 6-(4-aminophenyl)-1,2-dihydro-2-oxonicotinic acid, 200 ml of acetic acid, and 10.5 ml (110 mmol) of acetic anhydride is heated at reflux for 4.5 hrs. The mixture is cooled and diluted with 150 ml of ether. The solid is filtered, washed with ether, and dried at 60° to give 13.6 g of 6-[4-(acetylamino)phenyl]-1,2-dihydro-2-oxonicotinic acid; mp>260°.

A mixture of 8.2 g (30 mmol) of the above pyridone acid, 6.7 g (41.3 mmol) of carbonyldiimidazole, and 120 ml of N,N-dimethylacetamide is stirred at 50–65° for 1 hr, and finally at room temperature for 30 min. The mixture is diluted with 120 ml of tetrahydrofuran and the solid filtered, washed with tetrahydrofuran and ether, and dried to give 8.6 g of 6-[4-(acetylamino)-phenyl]-1,2-dihydro-2-oxonicotinic acid imidazolide.

A suspension of 9.0 g (20 mmol) of ampicillin triethylamine salt and 160 ml of N,N-dimethylacetamide is stirred at 0°–5° and 5.1 ml (40 mmol) chlorotrimethylsilane and 2.8 ml (20 mmol) of triethylamine is added. The ice bath is removed and the mixture is stirred at room temperature for 45 min. The mixture is cooled to 0°–5° and 6.44 g (20 mmol) of the above imidazolide is added. The reaction is stirred at 0°–5° for 15 min and stored at 0° overnight. A 1.5 L portion of ether is added and the solid is filtered and washed with ether. The solid is suspended in water and dissolved by adjusting to pH 8 with 1 N sodium hydroxide. The solution is acidified to pH 3 with hydrochloric acid and the precipitate is filtered, washed with water and ether, and dried under high vacuum. The crude product is treated with 80 ml of N,N-dimethylacetamide and filtered and 5 ml (14 mmol) of 2.8 M sodium 2-ethylhexanoate in n-butanol is added followed by 350 ml of ethyl acetate. The resulting solid is filtered, washed with ethyl acetate and ether, dissolved in 100 ml of water and lyophilized to give 6.05 g of the title penicillin as the sodium salt; $[\alpha]_D^{23} + 181°$ (cl, 75% dimethylformamide/pyridine).

| $E_1^1$ 460 | λ | 356 nm | |
|---|---|---|---|
| 138 | | 261 | pH 7 |

EXAMPLE 2

N-[6-[4-(acetylamino)phenyl]-1,2-dihydro-2-oxonicotinoyl]amoxicillin

A suspension of 12.3 g (21 mmol) of amoxicillin dimethyl sulfoxide complex and 240 ml of N,N-dimethylacetamide is stirred at 0°–5° and 6.4 g (20 mmol) of the imidazolide from Example 1 is added followed by 2.66 ml (19 mmol) of triethylamine. The ice bath is removed and the mixture is stirred overnight at room temperature. Insolubles are removed by filtration and the filtrate is poured into 1.2 L of ice and water. The pH is adjusted to 2 with 1 N hydrochloric acid and the precipitate filtered, resuspended in water and filtered again. The solid is suspended in 200 ml of water at 0°–5° and dissolved by adjusting the pH to 6 with 1 N sodium hydroxide. The solution is clarified by filtration and the filtrate is lyophilized to give 8.5 g of yellow solid. This material is combined with material from other runs. A total of 26.2 g is purified by fractional precipitation using methanol, tetrahydrofuran, and ether. A fraction of 6.0 g is dissolved in 30 ml of water and the hazy solution centrifuged. The clear supernatant liquid is lyophilized to give 4.6 g of the title penicillin as the sodium salt; $[\alpha]_D^{23} + 214°$ (cl, 75% dimethylformamide/pyridine).

| $E_1^1$ 455 | $\lambda$ | 356 nm | |
|---|---|---|---|
| 161 | | 261 | pH 7 |

EXAMPLE 3

N-[6-[4(Trifluoroacetylamino)phenyl]-1,2-dihydro-2-oxonicotinoyl]ampicillin

A suspension of 13.8 g (60 mmol) of 6-(4-aminophenyl)-1,2-dihydro-2-oxonicotinic acid, 25.2 ml (180 mmol) of triethylamine, and 600 ml of dichloromethane is stirred at 0°–5° and 24.0 ml (189 mmol) of chlorotrimethylsilane is added. The reaction mixture is stirred at room temperature for 1 hr and is cooled with a dry ice-acetone bath and 9.3 ml (66 mmol) of trifluoroacetic anhydride is added. The solution is stirred overnight while warming to room temperature. The dichloromethane is evaporated and water is added. The solid is filtered, washed with water and ether, and dried to give 19.8 g of 6-[4-(trifluoroacetylamino)phenyl]-1,2-dihydro-2-oxonicotinic acid; mp>270°.

A mixture of 16.3 g (50 mmol) of the above pyridone acid, 12.2 g (75 mmol) of carbonyldiimidazole, and 150 ml of N,N-dimethylacetamide is stirred at 55°–60° for 1 hr and at room temperature for 1 hr. The solid is filtered, washed with 150 ml of tetrahydrofuran, and dried to give 16.0 g of 6-[4-trifluoroacetylamine)phenyl]-1,2-dihydro-2-oxonicotinic acid imidazolide.

A suspension of 11.34 g (25.1 mmol) of ampicillin triethylamine salt and 100 ml of N,N-dimethylacetamide is stirred at 0°–5° and 7.05 ml (55.6 mmol) of chlorotrimethylsilane is added followed by 4.21 ml (30.1 mmol) of triethylamine. The ice bath is removed and the mixture is stirred at room temperature for 20 min. The reaction is cooled to 0°–5° and 6.3 g (16.7 mmol) of the above imidazolide is added and the resulting mixture is stirred overnight at room temperature. The mixture is poured into 600 ml of water and filtered. The pH of the filtrate is adjusted to 2.4 with 6.7 N hydrochloric acid and the resulting solid is collected by centrifugation, washed with water and centrifuged again. The solid is suspended in 200 ml of cold water and dissolved by adjusting the pH to 7 with 1 N sodium hydroxide. The solution is clarified by filtration and the filtrate is lyophilized to give 12.47 g of crude sodium salt. An 11.53 g portion of the salt is dissolved in 50 ml of cold methanol and filtered. The filtrate is treated with 125 ml of isopropanol and the resulting precipitate is isolated by centrifugation, washed with isopropanol and ether, and dissolved in water. The pH is adjusted to 7.0 and the solution lyophilized to give 5.7 g of the title penicillin as the sodium salt; $[\alpha]_D^{23} + 155°$ (cl, methanol).

| $E_1^1$ 386 | $\lambda$ | 355 nm | |
|---|---|---|---|
| 163 | | 267 | pH 7 |

EXAMPLE 4

N-[6-[4-(Trifluoroacetylamino)phenyl]-1,2-dihydro-2-oxonicotinoyl]amoxicillin

A suspension of 6.3 g (15 mmol) of amoxicillin trihydrate and 200 ml of N,N-dimethylacetamide is stirred at −10° and 11.4 ml (90 mmol) of chlorotrimethylsilane and 12.6 ml (90 mmol) of triethylamine are added. The mixture is stirred at room temperature for 1 hr and 5.64 g (15 mmol) of the imidazolide from Example 3 is added. The reaction is stirred at room temperature for 4 hrs and then is stored at 0° overnight. The mixture is filtered, washed with water and ether, and dried to give 9.3 g of crude product. The solid is dissolved in 93 ml of N,N-dimethylacetamide and 18.6 ml (15.4 mmol) of 0.83 M sodium 2-ethylbutyrate in tetrahydrofuran is added. The solution is poured into 500 ml of ethyl acetate and the precipitated solid is filtered. The gummy material is dissolved in water, filtered and the filtrate lyophilized to give 8.85 g of crude sodium salt. The salt is further purified by dissolving in 90 ml of cold methanol, adding 90 ml of isopropanol, 320 ml of ether, and filtering. The solid is dissolved in 150 ml of water and filtered. The filtrate is lyophilized to give 6.4 g of the title penicillin as the sodium salt; $[\alpha]_D^{23} + 184°$ (cl, 75% dimethylformamide/pyridine).

| $E_1^1$ 388 | $\lambda$ | 354 nm | |
|---|---|---|---|
| 174 | | 270 | pH 7 |

EXAMPLE 5

N-[6-[4-Cyanoacetylamino)phenyl]-1,2-dihydro-2-oxonicotinoyl]amoxicillin

Using the method for the preparation of the side chain acid in Example 3, 11.5 g (50 mmol) of 6-(4-aminophenyl)-1,2-dihydro-2-oxonicotinic acid, 500 ml of dichloromethane, 21.0 ml (150 mmol) of triethylamine, 20 ml (158 mmol) of chlorotrimethylsilane, and 5.67 g (55 mmol) of cyanoacetyl chloride [Org. Syn. Col. Vol. V p. 171] gives 14.7 g of 6-[4-(cyanoacetylamino)-phenyl]-1,2-dihydro-2-oxonicotinic acid; mp>280°.

A mixture of 8.6 g (28.7 mmol) of the above pyridone acid, 5.15 g (31.7 mmol) of carbonyldiimidazole, and 150 ml of N,N-dimethylacetamide is stirred at 50° for 30 min and at room temperature for 3 hrs. An equal volume of tetrahydrofuran is added and the mixture is stored in the refrigerator overnight. The solid is filtered, washed with ether, and dried under vacuum to give 6.5 g of 6-[4-(cyanoacetylamino)phenyl]-1,2-dihydro-2-oxonicotinic acid imidazolide.

A solution of 14.6 g (22 mmol) of amoxicillin dimethyl sulfoxide complex and 80 ml of N,N-dimethylacetamide is stirred at 0°–5° and 6.94 g (20 mmol) of the above imidazolide is added followed by 3 ml (22 mmol) of triethylamine. The ice bath is removed and the mixture stirred at room temperature for 4 hrs. The N,N-dimethylacetamide solution is added to 500 ml of ether and 300 ml ethyl acetate to give a gummy precipitate which solidifies. The solid is broken up, filtered, and dissolved in water. The pH is adjusted to 2.5 with 1 N hydrochloric acid and the resulting precipitate filtered. The solid is suspended in 500 ml cold water, filtered, and resuspended in 400 ml cold water. The pH is adjusted to 6.2, some insolubles filtered and the filtrate lyophilized to give 12.3 g of crude sodium salt.

This material is purified by dissolving in 300 ml water and adjusting to pH 2.5 with hydrochloric acid. The solid is filtered and resuspended in 120 ml of ice water and the pH adjusted to 5.5 and the clear solution lyophilized to give 9.5 g of solid. This is combined with 11.0 g, from another run, dissolved in 100 ml of water, and centrifuged at 9000 rpm for 30 min. The clear supernatant liquid is lyophilized and the solid further dried under high vacuum over phosphorus pentoxide to give 18.3 of the title penicillin as the sodium salt; $[\alpha]_D^{23}$ +215° (cl, 75% dimethylformamide/pyridine).

| $E_1^1$ 423 | $\lambda$ | 359 nm | |
|---|---|---|---|
| 170 | | 269 | pH 7 |

EXAMPLE 6

N-[6-[4-(1H-tetrazol-5-ylacetyl)amino]phenyl]-1,2-dihydro-2-oxonicotinoyl]amoxicillin A mixture of 13.4 g (45 mmol) of 6-(4-cyanoacetylaminophenyl)-1,2-dihydro-2-oxonicotinic acid from Example 5, 130 ml of dimethylformamide, 6.3 ml (45 mmol) of triethylamine, 9.75 g (150 mol) of sodium azide, and 8.03 g (150 mmol) of ammonium chloride is heated on the steam bath for 48 hrs. The reaction mixture is diluted with 600 ml of methanol and the resulting solution slowly acidified with 90 ml of 2 N hydrochloric acid. The precipitated solid is filtered, washed with methanol, and dried under vacuum at 60° for 24 hours to give 12.3 g of 6-[4-[(1H-tetrazol-5-ylacetyl)amino]phenyl]-1,2-dihydro-2-oxonicotinic acid.

A solution of 3.3 g (10 mmol) of the above pyridone acid, 3.2 g (20 mmol) of carbonyldiimidazole, and 15 ml of N,N-dimethylacetamide is stirred at room temperature for 5 hours. The reaction solution is poured into 130 ml of ethyl acetate and stirred for 15 minutes. The solid is filtered, washed with ethyl acetate, and dried under high vacuum over phosphorus pentoxide to give 3.5 g of 6-[4-[(1H-tetrazol-5-ylacetyl)amino]phenyl]-1,2-dihydro-2-oxonicotinic acid imidazolide.

A suspension of 6.3 g (10 mmol) of amoxicillin dimethyl sulfoxide complex and 75 ml of N,N-dimethylacetamide is stirred at 0°–5° and 1.12 ml (8 mmol) of triethylamine is added followed by 5 g (ca. 9 mmol) of the above imidazolide. The reaction mixture is stirred at 0°–5° for 4 hrs and 7.7 ml (25 mmol) of 3.3 M sodium 2-ethylhexanoate in N,N-dimethylacetamide is added. The solution is poured into 300 ml of ethyl acetate and the precipitated solid filtered and washed with ethyl acetate. The solid is dissolved in 300 ml of ice cold water and the pH is adjusted to 2.4 with 1 N hydrochloric acid. The precipitate is filtered, resuspended in 200 ml of water, and the pH adjusted to 7 with 1 N sodium hydroxide. Filtration and lyophilization gives 6.7 g of the disodium salt of the title penicillin; $[\alpha]_D^{23}$ −234° (cl, pH 7).

| $E_1^1$ 358 $\lambda$ 358 nm pH 7 |
|---|

EXAMPLE 7

N-[6-[4-(1,2-Dioxopropylamino)phenyl]-1,2-dihydro-2-oxonicotinoyl]amoxicillin

Using the method for the preparation of the side chain acid in Example 3, 11.5 g (50 mmol) of 6-(4-aminophenyl)-1,2-dihydro-2-oxonicotinic acid, 500 ml of dichloromethane, 21.0 ml (150 ml) of triethylamine, 20 ml (158 mmol) of chlorotrimethylsilane, and 8.0 g (75 mmol) of pyruvic acid chloride, [J. Org. Chem., 35, 3972 (1970)] gives 6.6 g of 6-[4(1,2-dioxopropylamino)-phenyl]-1,2-dihydro-2-oxonicotinic acid after recrystallization from N,N-dimethylacetamide; mp>280°.

A mixture of 5.0 g (16.6 mmol) of the above pyridone acid, 3.24 g (20 mmol) of carbonyldiimidazole, and 100 ml of N,N-dimethylacetamide is stirred at 60° for 1 hr and at room temperature for 2 hrs. The mixture is filtered, the solid washed with ether, and dried under vacuum overnight at 40° to give 5.1 g of 6-[4-(1,2-dioxopropylamino)phenyl]-1,2-dihydro-2-oxonicotinic acid imidazolide.

A solution of 4.4 g (6.6 mmol) of amoxicillin dimethyl sulfoxide complex and 30 ml of N,N-dimethylacetamide is stirred at 0°–5° and 2.1 g (6 mmol) of the above imidazolide and 30 ml of dimethyl sulfoxide are added. The ice bath is removed and the mixture is stirred at room temperature for 3 hrs and 0.8 ml (6 mmol) of triethylamine is added. Stirring is continued for 2 hrs and the reaction mixture is stored in the refrigerator overnight. The mixture is filtered and the filtrate is kept at room temperature for 3 hrs and 300 ml ethyl acetate and 200 ml ether are added producing a gummy precipitate. The mixture is extracted with water and the pH of the aqueous is adjusted to 2.7 with 1 N hydrochloric acid and the precipitate filtered. The solid is suspended in 200 ml of ice water, filtered, resuspended in 100 ml of water, and the pH adjusted to 6.0 with 1 N sodium hydroxide. The solution is clarified by filtration and the filtrate lyophilized to give 2.8 g of the sodium salt of the title penicillin; $[\alpha]_D^{23}$ +176° (c 0.98, 75% dimethylformamide/pyridine).

| $E_1^1$ 392 | $\lambda$ | 358 nm | |
|---|---|---|---|
| 135 | | 273 | pH 7 |

EXAMPLE 8

N-[6-[4-(2,2,2-Trifluoroethyl)thio]acetylamino]phenyl]-1,2-dihydro-2-oxonicotinoyl]amoxicillin Using the method for the preparation of the side chain acid in Example 3, 4.62 g (20 mmol) of 6-(4-aminophenyl)-1,2-dihydro-2-oxonicotinic acid, 8.4 ml (60 mmol) of triethylamine, 200 ml of dichloromethane, 8.0 ml (63 mmol) of chlorotrimethylsilane, and 4.4 g (23 mmol) of 2-[2,2,2-trifluoroethyl)thio]acetyl chloride [J. Med. Chem., 20, 30 (1977)] gives 7.3 g of 6-[4-[(2,2,2-trifluoroethyl)thio]acetylamino]phenyl-1,2-dihydro-2-oxonicotinic acid; mp>300°.

A mixture of 7.00 g (18 mmol) of the above pyridone acid, 5.8 g (36 mmol) of carbonyldiimidazole, and 40 ml of N,N-dimethylacetamide is stirred at 40°–45° for 45 min and at room temperature for 45 minutes. The reaction is diluted with 40 ml ethyl acetate and filtered. The solid is washed with ethyl acetate and dried under high vacuum over phosphorus pentoxide to give 6.4 g of 6-[4-[(2,2,2-trifluoroethyl)thio]acetylamino]phenyl-1,2-dihydro-2-oxonicotinic acid imidazolide.

A solution of 2.60 g (4.12 mmol) amoxicillin dimethyl sulfoxide complex, 1.80 g (4.12 mmol) of the above imidazolide, and 15 ml of N,N-dimethylacetamide is stirred at room temperature and 0.55 ml (4.0 mmol) of triethylamine is added. After 45 min the reaction mixture is poured into 150 ml of ice water containing 4 ml 1 N hydrochloric acid. The resulting solution is acidified to pH 2.5 with 1 N hydrochloric acid and the precipitate filtered, stirred with 100 ml of ice water, and refiltered. The solid is suspended in 100 ml ice water and dissolved by addition of 1 N sodium hydroxide. The solution is lyophilized to give 2.7 g of the sodium salt of the title penicillin; $[\alpha]_D^{23} + 176°$ (cl, 75% dimethylformamide/pyridine).

| $E_1^1$ 377 | λ | 358 nm | |
|---|---|---|---|
| 370 | | 142 | pH 7 |

EXAMPLE 9

N-[6-[4-[(Cyanomethyl)thio]acetylamino]phenyl]-1,2-dihydro-2-oxonicotinoyl]amoxicillin A suspension of 4.6 g (20 mmol) of 6-(4-aminophenyl)-1,2-dihydro-2-oxonicotinic acid and 200 ml of dichloromethane is stirred at 0°–5° and 7.7 ml of (60 mmol) chlorotrimethylsilane is added followed by 11.2 ml (80 mmol) of triethylamine. The ice bath is removed and the mixture stirred at room temperature for 30 min. The reaction mixture is cooled to −5° and a solution of 40 mmol of the mixed anhydride of cyanomethylmercaptoacetic acid and trimethylacetyl chloride in 200 ml of methylene chloride [Arzeim-Forsch Drug Res., 27, 351 (1977)] is added during a 30 min period followed by 2.8 ml (20 mmol) of triethylamine. The reaction mixture is stirred at 0°–5° for 2 hr and allowed to stand overnight at room temperature. The dark solution is extracted with water and a solid separates. The solid is filtered and the aqueous layers are concentrated and additional solid is isolated. The pH of the aqueous filtrate is adjusted to 2.5 and a third crop is obtained. The three crops are combined and dissolved in 50 ml of N,N-dimethylacetamide and precipitated with methanol to give 4.11 g of 6-[4-[(cyanomethyl)thio]acetylamino]phenyl-1,2-dihydro-2-oxonicotinic acid; mp>280°.

A mixture of 4.11 g (12 mmol) of the above pyridone acid, 2.9 g (18 mmol) of carbonyldiimidazole, and 30 ml of N,N-dimethylacetamide is stirred at 55° for 30 min and at room temperature for 2 hrs. The mixture is diluted with 30 ml of tetrahydrofuran and stored in the refrigerator overnight. The solid is filtered, washed with ether, and dried under vacuum overnight to give 3.58 g of 6-[4-[(cyanomethyl)thio]acetylamino]phenyl-1,2-dihydro-2-oxonicotinic acid imidazolide.

A solution of 3.5 g (5.5 mmol) of amoxicillin dimethyl sulfoxide complex and 20 ml of N,N-dimethylacetamide is stirred at 0°–5° and 1.96 g (5 mmol) of the above imidazolide is added followed by 0.7 ml (5 mmol) of triethylamine. The mixture is stirred at 0°–5° for 30 min, 30 min at room temperature, and 1 hr at 0°–5°. The solution is added to 100 ml of ice water containing 5 ml of 1 N hydrochloric acid. The pH is adjusted to 2.5 with 1 N hydrochloric acid and the precipitate is collected by filtration. The solid is suspended in cold water, filtered, and resuspended in 50 ml of water and the pH adjusted to 6.0 with 1 N sodium hydroxide. The solution is clarified by filtration and the filtrate is lyophilized to give 2.9 g of the title penicillin as the sodium salt; $[\alpha]_D^{23} + 194°$ (cl, 75% dimethylformamide/pyridine).

| $E_1^1$ 422 | λ | 360 nm | |
|---|---|---|---|
| 164 | | 271 | pH 7 |

EXAMPLE 10

N-[6-[4-[(2-Ethoxy-1,2-dioxoethyl)amino]phenyl]-1,2-dihydro-2-oxonicotinoyl]amoxicillin A suspension of 1.96 g (8.5 mmol) of 6-(4-aminophenyl)-1,2-dihydro-2-oxonicotinic acid and 85 ml of dichloromethane is stirred at room temperature and 3.19 ml (25.5 mmol) of chlorotrimethylsilane is added followed by 3.57 ml (25.5 mmol) of triethylamine. The reaction mixture is stirred for 15 min at room temperature and 0.75 ml (8.5 mmol) of ethyl oxalyl chloride is added followed by 1.19 ml (8.5 mmol) of triethylamine. The solution is stirred at room temperature for 15 min and another millimole each of the oxalyl chloride and triethylamine are added. The reaction is stirred at room temperature for 30 min, filtered, and the filtrate evaporated to dryness under reduced pressure. The residue is dissolved in 80 ml of cold water and acidified to pH 2.1 with hydrochloric acid. The precipitated solid is filtered, washed with water, and dried under high vacuum to give 2.9 g of 6-[4-[(2-ethoxy-1,2-dioxoethyl)amino]phenyl]-1,2-dihydro-2-oxonicotinic acid.

A mixture of 2.97 g (9 mmol) of the above pyridone acid, 2.35 g (14.5 mmol) of carbonyldiimidazole, and 45 ml of dimethylformamide is stirred at 60° for 10 min and 2 hrs at room temperature. The reaction is diluted with 50 ml of ether and the solid is filtered, washed with ether, and dried to give 2.65 g of 6-[4-[(2-ethyoxy-1,2-dioxoethy)amino]phenyl]-1,2-dihydro-2-oxonicotinic acid imidazolide.

A suspension of 3.2 g (5.3 mmol) of amoxicillin dimethyl sulfoxide complex and 25 ml of dimethyl sulfoxide is stirred at room temperature and 0.74 ml (5.3 mmol) of triethylamine is added followed by 1.64 g (4.4 mmol) of the above imidazolide. The solution is stirred at room temperature for 2.5 hrs and poured into 160 ml of ice water. The pH is adjusted to 2.5 with hydrochloric acid and the precipitated solid is filtered, washed with ice water, resuspended in water and dissolved by adjusting the pH to 6.8 with aqueous sodium hydroxide. The solution is clarified by filtration and the filtrate lyophilized to give 2.85 g of the title penicillin as the sodium salt; $[\alpha]_D^{25} - 114°$ (cl, pH 7).

| $E_1^1$ 432 | λ | 358 nm | |
|---|---|---|---|
| 161 | | 276 | pH 7 |

EXAMPLE 11

N-[6-[4-(Benzyloxycarbonylamino)phenyl]-1,2-dihydro-2-oxonicotinoyl]ampicillin

A suspension of 6.9 g (30 mmol) of 6-(4-aminophenyl)-1,2-dihydro-2-oxonicotinic acid, 10 g (100 mmol) of potassium bicarbonate, and 100 ml of water is stirred at room temperature and 300 ml of dimethylformamide is added followed by 6.0 ml (43 mmol) of benzyl chloroformate. The mixture is stirred at room temperature for 2 hrs and 6.0 ml of benzyl chloroformate and 6.0 g of potassium bicarbonate are added. The reaction is stirred overnight at room temperature and poured into 700 ml of ice water. The pH is adjusted to 3 with hydrochloric acid and the precipitate is filtered, washed with water, and dried to give 9.44 g of 6-[4-(benzyloxycarbonylamino)phenyl]-1,2-dihydro-2-oxonicotinic acid after recrystallization from N,N-dimethylacetamide-methanol.

A mixture of 7.27 g (20 mmol) of the above pyridone acid, 4.3 g (26.5 mmol) of carbonyldiimidazole, and 80 ml of dimethylformamide is stirred at 60° for 15 min, and allowed to stand at room temperature for 2 hrs. The reaction is warmed to 60° for 15 min, cooled to 0°–5°, and filtered. The solid is washed with dimethylformamide and ether and dried under vacuum to give 6.2 g of 6-[4-(benzyloxycarbonylamino)phenyl]-1,2-dihydro-2-oxonicotinic acid imidazolide.

A suspension of 6.8 g (15 mmol) of ampicillin triethylamine salt and 60 ml of dimethylformamide is stirred at room temperature and 4.2 ml (33 mmol) of chlorotrimethylsilane is added followed by 2.25 ml (17 mmol) of triethylamine. The reaction mixture is stirred at room temperature for 30 min and 6.2 g (15 mmol) of the above imidazolide is added. Stirring is continued for 3 hrs at room temperature and the reaction mixture is poured into water and the pH is adjusted to 6.5 with aqueous sodium hydroxide. The solution is extracted three times with ethyl acetate and stored in the refrigerator overnight. The pH of the hazy aqueous solution is lowered to 2.5 with hydrochloric acid. The precipitated solid is washed with water and dried under high vacuum to give 9.06 g of orange solid. A 0.5 g portion of this material is suspended in water and dissolved by adjusting the pH to 6.3 with aqueous sodium hydroxide. Filtration and lyophilization gives 450 mg of the title penicillin as the sodium salt.

$E_1^1$ 311 λ 362 nm pH 7

EXAMPLE 12

N-[6-[4-(Methoxycarbonylamino)phenyl]-1,2-dihydro-2-oxonicotinoyl]amoxicillin

Using the method for the preparation of the side chain acid in Example 3, 4.62 g (20 mmol) of 6-(4-aminophenyl)-1,2-dihydro-2-oxonicotinic acid, 8.4 ml (60 mmol) of triethylamine, 8.0 ml (63 mmol) of chlorotrimethylsilane, 200 ml of dichloromethane, and 2.5 ml (30 mmol) of methyl chloroformate gives 5.04 g of 6-[4-(methoxycarbonylamino)phenyl]-1,2-dihydro-2-oxonicotinic acid.

A mixture of 3.8 g (13.2 mmol) of the above pyridone acid, 3.0 g (18.5 mmol) of carbonyldiimidazole, and 65 ml of dimethyl sulfoxide is stirred at 50°–60° for 3 hrs and at room temperature overnight. The reaction mixture is treated with 60 ml dichloromethane and 50 ml of ether and the solid is filtered, washed with dichloromethane and ether, and dried to give 3.06 g of 6-[4-(methoxycarbonylamino)phenyl]-1,2-dihydro-2-oxonicotinic acid imidazolide.

A suspension of 5.4 g (9 mmol) of amoxicillin dimethyl sulfoxide complex and 45 ml of dimethyl sulfoxide is stirred at room temperature and 1.25 ml (9 mmol) of triethylamine is added followed by 2.7 g (8 mmol) of the above imidazolide. The reaction mixture is stirred at room temperature for 9.5 hrs and is poured into 300 ml of ice water. The pH is lowered to 2.5 with hydrochloric acid and the precipitated solid filtered, washed with water and suspended in water. The solid is brought into solution by raising the pH to 6.3 with 1 N sodium hydroxide. The solution is filtered and the filtrate lyophilized to give 5.5 g of the sodium salt of the title penicillin; $[\alpha]_D^{23}$ −470° (c1, pH 7).

$E_1^1$ 430 λ 362 nm pH 7

EXAMPLE 13

N-[6-[4-(Phenylacetylamino)phenyl]-1,2-dihydro-2-oxonicotinoyl]amoxicillin

A suspension of 6.9 g (30 mmol) of 6-(4-aminophenyl)-1,2-dihydro-2-oxonicotinic acid, 12.6 ml (90 mmol) of triethylamine, and 300 ml of dichloromethane is stirred at 0°–5° and 12 ml (94.5 mmol) of chlorotrimethylsilane is added. The reaction mixture is stirred at room for 1 hr and is cooled with a dry ice-acetone bath and 4.6 ml (35 mmol) of phenylacetyl chloride is added. The solution is stirred overnight while warming to room temperature. The dichloromethane is evaporated and water is added. The solid is filtered, washed with water and ether, and dried to give 7.0 g of 6-[4-(phenylacetylamino)phenyl]-1,2-dihydro-2-oxonicotinic acid; mp>280° after crystallization from 100 ml of N,N-dimethylacetamide.

A mixture of 4.35 g (10 mmol) of the above pyridone acid, 2.3 g (14 mmol) of carbonyldiimidazole, and 30 ml of N,N-dimethylacetamide is stirred at 60° for 40 min and at room temperature for 3 hrs. After standing overnight at room temperature the reaction mixture is diluted with 250 ml of tetrahydrofuran and filtered. The solid is washed with ether and dried under high vacuum over phosphorus pentoxide to give 3.0 g of 6-[4-(phenylacetylamino)phenyl]-1,2-dihydro-2-oxonicotinic acid imidazolide.

A solution of 5.78 g (8.82 mmol) of amoxicillin dimethyl sulfoxide complex and 200 ml of N,N-dimethylacetamide is cooled with an ice salt bath and 3.0 g (8.4 mmol) of the above imidazolide is added. The reaction mixture is stirred in the ice bath for 3 hrs and is refrigerated overnight. The solution is added to 1 L of ice water and the hazy solution clarified by filtration. The filtrate is acidified to pH 2.75 with 1 N hydrochloric acid. The precipitate is filtered, washed with water, and dried over phosphorus pentoxide under high vacuum. The solid is dissolved in 100 ml of cold N,N-dimethylacetamide and the insolubles filtered off. The filtrate is treated with 4.3 ml of sodium 2-ethylhexanoate (50% in n-butanol) followed by 400 ml of ethyl ether. The precipitate is filtered and washed with ether and dried under high vacuum overnight. The solid is dissolved in 60 ml of ice water and lyophilized to give 5.0 g of the sodium salt of the title penicillin;

$E_1^1$ 226 λ 348 nm pH 7

EXAMPLE 14

N-[6-[4-(N-Ethylcarbamoylamino)phenyl]-1,2-dihydro-2-oxonicotinoyl]amoxicillin

A suspension of 9.2 g (40 mmol) of 6-(4-aminophenyl)-1,2-dihydro-2-oxonicotinic acid, 100 ml of dimethylformamide, 4.8 ml (60 mmol) of ethyl isocyanate and 5.6 ml (40 mmol) of triethylamine is stirred at 25° for 16 hrs. The dimethylformamide is evaporated under reduced pressure and the residue is treated with 200 ml of water and the pH is adjusted to 2.0 with 1 N hydrochloric acid. The solid is filtered and washed with methanol, ether and dried to give 11.8 g of 6-[4-(N-ethylcarbamoylamino)phenyl]-1,2-dihydro-2-oxonicotinic acid.

A suspension of 9.8 g (32.6 mmol) of the above acid, 10.5 g (65 mmol) of carbonyldiimidazole and 50 ml of dimethylformamide is stirred at room temperature for 6 hrs. The reaction mixture is diluted with 200 ml of ethyl acetate and the solid is filtered and dried to give 12.3 g of 6-[4-(N-ethylcarbamoylamino)phenyl]-1,2-dihydro-2-oxonicotinic acid imidazolide.

A suspension of 7.6 g (11 mmol) of amoxicillin dimethyl sulfoxide complex, 3.51 g (10 mmol) of the above imidazolide, and 50 ml of N,N-dimethylacetamide is stirred at 0°–5° and 1.4 ml (10 mmol) of triethylamine is added. The reaction mixture is stirred at 0°–5° for 20 min and at 25° for 4 hrs and 3.3 ml (10 mmol) of 3 M sodium 2-ethylhexanoate in N,N-dimethylacetamide is added. The resulting solution is added to 800 ml of ethyl acetate over a 20 min period. The solid is filtered, washed, dried, and dissolved in 200 ml of ice water and the pH of the solution is adjusted to 2.5 with 1 N hydrochloric acid. The precipitated solid is filtered and washed with water and resuspended in 100 ml of ice water. The pH of the suspension is adjusted to 6.5 and the resulting solution is lyophilized to give 5.45 g of the title penicillin as the sodium salt; $[\alpha]_D^{23} -435°$ (cl, pH 7).

$E_1^1$ 425 λ 365 nm pH 7

EXAMPLE 15

N-[6-[3-(Acetylamino)phenyl]-1,2-dihydro-2-oxonicotinoyl]ampicillin

A mixture of 4.6 g (20 mmol) of 6-(3-aminophenyl)-1,2-dihydro-2-oxonicotinic acid and 100 ml of acetic anhydride is stirred at reflux for 2 hrs. The reaction is cooled and the solid filtered, washed with acetonitrile and ether, and dried to give 4.12 of 6-[3(acetylamino)-phenyl]-1,2-dihydro-2-oxonicotinic acid.

A suspension of 3.81 g (14 mmol) of the above pyridone acid and 100 ml of thionyl chloride is stirred at 45° for 1 hr and at room temperature overnight. The reaction mixture is stirred for 3 hrs at 52°, cooled, and filtered. The solid is washed with hexane and dried under high vacuum over phosphorus pentoxide to give 3.57 g of 6-[3-(acetylamino)phenyl]-1,2-dihydro-2-oxonicotinoyl chloride.

A suspension of 3.15 g (7 mmol) of ampicillin triethylamine salt and 100 ml of tetrahydrofuran is stirred at 0°–5° and 1.8 ml (14 mmol) of chlorotrimethylsilane is added followed by 3.0 ml (21 mmol) of triethylamine. The ice bath is removed and the reaction stirred at room temperature for 15 min. The mixture is cooled to 0°–5° and 2.04 g (7 mmol) of the above acid chloride is added and the reaction mixture is stirred at room temperature for 5 hrs. The suspension is filtered and the filtrate evaporated under reduced pressure. The residue is treated with 150 ml of water and the pH is adjusted to 8.5 with 1 N sodium hydroxide. The solution is clarified by filtration and the pH of the filtrate is adjusted to 4 with hydrochloric acid. The precipitated solid is filtered, washed with water and dried to give 0.2 g of the title penicillin; $[\alpha]_D^{23} +182°$ (cl, 75% dimethylformamide/pyridine).

$E_1^1$ 314 λ 350 nm DMF-pH 7

STARTING MATERIALS

A. 6-(4-Aminophenyl)-1,2-dihydro-2-oxonicotinic acid

A suspension of 330 g (6.1 mol) of sodium methoxide, 3 L of tetrahydrofuran, and 2.5 L of ether is stirred at room temperature and a suspension of 490 g (2.77 mol) of 4-(acetylamino)acetophenone, 416 g (5.54 mol) of ethyl formate, and 3 L of tetrahydrofuran is added over a period of 1 hr. The suspension is stirred at room temperature overnight under nitrogen. The precipitate is allowed to settle and the solvent drawn off with a filter candle. Another 3 L of tetrahydrofuran is added and the solvent again removed by filter candle.

Water (9 L) is added to the residue and the pH is adjusted to 9.0 with glacial acetic acid and 388 g (4.6 mol) of 2-cyanoacetamide is added. The mixture is warmed to 90° on a steam bath while allowing the residual tetrahydrofuran and ether to escape. The system is fitted with a condenser and heated at this temperature overnight. The suspension is cooled and the pH is adjusted to 5.8 with acetic acid. The brown solid is filtered and washed with water, 1:1 methanol water, methanol and finally ethyl acetate. Drying affords 422 g of 6-(4-acetylaminophenyl)-1,2-dihydro-2-oxonicotinonitrile; mp > 350°.

A suspension of 422 g (1.67 mol) of the above nitrile and 3650 ml of water containing 932 g of potassium hydroxide is heated at 105° for 40 hrs. The solution is cooled and acidified to pH 4.0 with 1360 ml of concentrated hydrochloric acid and 400 g of potassium hydroxide pellets are added with stirring. After filtration, the pH of the filtrate is adjusted to 4.5 with concentrated hyrochloric acid. The solid is filtered, suspended in 8 L of water and filtered. The solid is washed with mthanol and finally ethyl acetate and dried at 60° to give 328 g of the title compound; mp 314°–316° dec.

$E_1^1$ 944 λ 347 nm pH 7

B. 6-(3-Aminophenyl)-1,2-dihydro-2-oxonicotinic acid

A stirred suspension of 71.3 g (1.32 mol) of sodium methoxide, 500 ml of tetrahydrofuran, and 300 ml of ether is cooled to 0°–5° under nitrogen and a solution of 106.3 g (0.6 mol) of 3-(acetylamino)acetophenone, 96.94 (1.2 ml) of ethyl formate, 700 ml of dry acetonitrile, and 350 ml of tetrahydrofuran is added during 30 min. The reaction is allowed to warm to room temperature with stirring overnight. The organic solvents are decanted from the solids and the solids dissolved in 2.25 L of water. The pH is adjusted to 9.0 with glacial acetic acid and 84.1 g (1.0 mol) of 2-cyanoacetamide is added. The solution is heated at reflux for 3.5 hrs, cooled, and filtered. The solids are washed with water, acetonitrile, and ether and dried to give 93.1 g of 6-(3-acetylaminophenyl)-1,2-dihydro-2-ononicotinonitrile; mp 326°–328°.

$E_1^1$ 768 λ 350 nm

| -continued | | |
|---|---|---|
| 890 | 242 | pH 7 |

A mixture of 92.5 g (0.37 mol) of the above nitrile, 185 g of potassium hydroxide, and 740 ml of water is heated at 105° for 30 hrs. The cooled reaction mixture is poured into 285 ml of concentrated hydrochloric acid and ice. The pH as the suspension is adjusted to 5.0 with aqueous sodium hydroxide solution and the solid filtered, washed with water, and dried to give 81.2 g of the title compound.

| $E_1^1$ 650 | λ | 329 nm | |
|---|---|---|---|
| 825 | | 227 | pH 7 |

We claim:

1. A compound of the formula

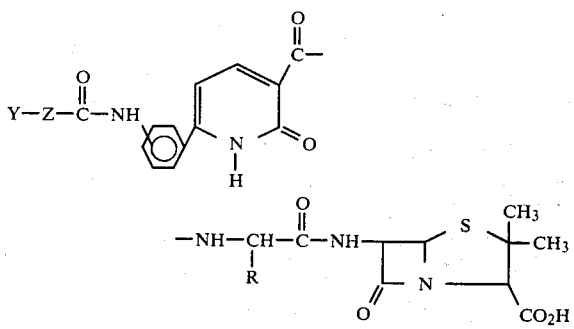

and pharmaceutically acceptable salts thereof; wherein Z is a single bond and Y is lower alkyl, benzyl, $CF_3$, lower alkyl amino, lower alkyl carbonyl, lower alkoxy carbonyl, benzyloxy, and lower alkoxy, where X is a methylene group and Y is cyano, tetrazolyl, $R^1$ $CH_2S$ where $R^1$ is $CF_3$ or CN and R is phenyl, 4-hydroxyphenyl, 2-thienyl or cyclohexa-1,4-dien-1-yl.

2. The compounds of claim 1 wherein

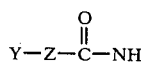

is in the p position and R is phenyl or 4-hydroxyphenyl.

3. A compound of claim 1 having the name N-[6-[4-(acetylamino)phenyl]-1,2-dihydro-2-oxonicotinoyl]ampicillin and pharmaceutically acceptable salts thereof.

4. A compound of claim 1 having the name N-[6-[4-(acetylamino)phenyl]-1,2-dihydro-2-oxonicotinoyl]amoxicillin and pharmaceutically acceptable salts thereof.

5. A compound of claim 1 having the name N-[6-[4-(trifluoroacetyl)phenyl]-1,2-dihydro-2-oxonicotinoyl]ampicillin and pharmaceutically acceptable salts thereof.

6. A compound of claim 1 having the name N-[6-[4-(trifluoroacetylamino)phenyl]-1,2-dihydro-2-oxonicotinoyl]amoxicillin and pharmaceutically acceptable salts thereof.

7. A compound of claim 1 having the name N-[6-[4-cyanoacetylamino)phenyl]-1,2-dihydro-2-oxonicotinoyl]amoxicillin and pharmaceutically acceptable salts thereof.

8. A compound of claim 1 having the name N-[6-[4-[(1H-tetrazol-5-ylacetyl)amino]phenyl]-1,2-dihydro-2-oxonicotinoyl]amoxicillin and pharmaceutically acceptable salts thereof.

9. A compound of claim 1 having the name N-[6-[4-(1,2-dioxopropylamino)phenyl]-1,2-dihydro-2-oxonicotinoyl]amoxicillin and pharmaceutically acceptable salts thereof.

10. A compound of claim 1 having the name N-[6-[4-[(2,2,2-trifluoromethyl)thio]acetylamino]phenyl]-1,2-dihydro-2-oxonicotinoyl]amoxicillin and pharmaceutically acceptable salts thereof.

11. A compound of claim 1 having the name N-[6-[4-[cyanomethyl)thio]acetylamino]phenyl]-1,2-dihydro-2-oxonicotinoyl]amoxicillin and pharmaceutically acceptable salts thereof.

12. A compound of claim 1 having the name N-[6-[4-[(2-ethoxy-1,2-dioxoethyl)amino]phenyl]-1,2-dihydro-2-oxonicotinoyl]amoxicillin and pharmaceutically acceptable salts thereof.

13. A compound of claim 1 having the name N-[6-[4-(benzyloxycarbonylamino)phenyl]-1,2-dihydro-2-oxonicotinoyl]ampicillin and pharmaceutically acceptable salts thereof.

14. A compound of claim 1 having the name N-[6-[4-(methoxycarbonylamino)phenyl]-1,2-dihydro-2-oxonicotinoyl]amoxicillin and pharmaceutically acceptable salts thereof.

15. A compound of claim 1 having the name N-[6-[4-(phenylacetylamino)phenyl]-1,2-dihydro-2-oxonicotinoyl]amoxicillin and pharmaceutically acceptable salts thereof.

16. A compound of claim 1 having the name N-[6-[4-(N-ethylcabamoylamino)phenyl]-1,2-dihydro-2-oxonicotinoyl]amoxicillin and pharmaceutically acceptable salts thereof.

17. A compound of claim 1 having the name N-[6-[3-(acetylamino)phenyl]-1,2-dihydro-2-oxonicotinoyl]ampicillin and pharmaceutically acceptable salts thereof.

18. A compound of the formula where Y and Z are as defined in claim 1 and X is cyano, carboxy, or a carboxylate salt.

* * * * *